(12) United States Patent
Sun et al.

(10) Patent No.: US 10,625,470 B2
(45) Date of Patent: Apr. 21, 2020

(54) 3D PRINTING OF COMPOSITION-CONTROLLED COPOLYMERS

(71) Applicant: ADA Foundation, Chicago, IL (US)

(72) Inventors: Jirun Sun, Rockville, MD (US); Young Lee, Gaithersburg, MD (US)

(73) Assignee: ADA FOUNDATION, Chicago, IL (US)

( * ) Notice: Subject to any disclaimer, the term of this patent is extended or adjusted under 35 U.S.C. 154(b) by 153 days.

(21) Appl. No.: 15/702,779

(22) Filed: Sep. 13, 2017

(65) Prior Publication Data

US 2018/0086002 A1 Mar. 29, 2018

Related U.S. Application Data

(60) Provisional application No. 62/400,967, filed on Sep. 28, 2016.

(51) Int. Cl.
*B29C 64/393* (2017.01)
*B33Y 70/00* (2020.01)
(Continued)

(52) U.S. Cl.
CPC .......... *B29C 64/393* (2017.08); *A61K 6/0002* (2013.01); *A61K 6/0052* (2013.01); *A61K 6/0073* (2013.01); *A61K 6/0088* (2013.01); *A61K 6/083* (2013.01); *B29C 64/00* (2017.08); *B29C 64/106* (2017.08); *B29C 64/336* (2017.08); *B29C 64/386* (2017.08); *B33Y 50/02* (2014.12); *B33Y 80/00* (2014.12);
(Continued)

(58) Field of Classification Search
CPC ..... B29C 64/393; B29C 64/106; B29C 64/00; B29C 64/386; B29C 64/336; B33Y 50/02; B33Y 80/00; A61K 6/0002; A61K 6/0052; A61K 6/0073; A61K 6/0088; A61K 6/083; C08K 3/22; C08K 3/36; C08K 5/08; C08K 5/18; G02B 1/041; C08J 9/0061

See application file for complete search history.

(56) References Cited

U.S. PATENT DOCUMENTS 4,575,330 A 3/1986 Hull
6,813,082 B2 * 11/2004 Bruns ................. B29C 35/0805
264/1.31

(Continued)

OTHER PUBLICATIONS

Zukauskas, et al., "Tuning the refractive index in 3D direct laser writing lithography: towards GRIN microoptics," Laser Photonics Rev. 9, No. 6, pp. 706-712, 2015, Wiley-VCH Verlag GmbH & Co. KGaA, Weinheim.

*Primary Examiner* — Mathieu D Vargot

(57) ABSTRACT

A computer-controlled method for forming a composition-controlled product using 3D printing includes disposing two or more liquid reactant compositions in respective two or more reservoirs; and mixing the two or more liquid reactant compositions, which in turn includes controlling by the computer a mass ratio of the mixed two or more liquid reactant compositions. The computer-controlled method further includes scanning, under control of the computer, a mixed liquid reactants nozzle over a substrate; depositing the mixed liquid reactant compositions onto the substrate; and operating, under control of the computer, a light source to polymerize the deposited mixed liquid reactant compositions.

19 Claims, 2 Drawing Sheets

(51) Int. Cl.

| | | |
|---|---|---|
| *B29C 64/386* | (2017.01) | |
| *C08J 9/00* | (2006.01) | |
| *B29C 64/00* | (2017.01) | |
| *B29C 64/336* | (2017.01) | |
| *B33Y 50/02* | (2015.01) | |
| *B33Y 80/00* | (2015.01) | |
| *B29C 64/106* | (2017.01) | |
| *A61K 6/00* | (2020.01) | |
| *A61K 6/083* | (2006.01) | |
| *C08K 3/22* | (2006.01) | |
| *C08K 5/08* | (2006.01) | |
| *C08K 5/18* | (2006.01) | |
| *G02B 1/04* | (2006.01) | |
| *B33Y 50/00* | (2015.01) | |
| *B33Y 30/00* | (2015.01) | |
| *B33Y 10/00* | (2015.01) | |
| *B29K 67/00* | (2006.01) | |
| *B29K 71/00* | (2006.01) | |
| *B29K 105/00* | (2006.01) | |
| *B29K 105/04* | (2006.01) | |
| *B29K 309/02* | (2006.01) | |
| *B29L 11/00* | (2006.01) | |
| *B29L 31/00* | (2006.01) | |
| *C08J 9/26* | (2006.01) | |
| *C08K 3/36* | (2006.01) | |

(52) U.S. Cl.
CPC ............... *C08J 9/0061* (2013.01); *C08K 3/22* (2013.01); *C08K 5/08* (2013.01); *C08K 5/18* (2013.01); *G02B 1/041* (2013.01); *B29K 2067/04* (2013.01); *B29K 2071/00* (2013.01); *B29K 2105/0002* (2013.01); *B29K 2105/0005* (2013.01); *B29K 2105/0085* (2013.01); *B29K 2105/04* (2013.01); *B29K 2309/02* (2013.01); *B29L 2011/0016* (2013.01); *B29L 2031/7532* (2013.01); *B33Y 10/00* (2014.12); *B33Y 30/00* (2014.12); *B33Y 50/00* (2014.12); *B33Y 70/00* (2014.12); *C08J 9/26* (2013.01); *C08J 2201/026* (2013.01); *C08J 2201/0422* (2013.01); *C08J 2201/0446* (2013.01); *C08J 2201/0462* (2013.01); *C08J 2207/10* (2013.01); *C08J 2329/10* (2013.01); *C08J 2335/02* (2013.01); *C08J 2425/06* (2013.01); *C08K 3/36* (2013.01); *C08K 2003/2227* (2013.01); *C08K 2003/2241* (2013.01); *G02B 1/04* (2013.01)

(56) References Cited

U.S. PATENT DOCUMENTS 7,420,743 B2 * 9/2008 Lai .................. B29D 11/00355
359/642
2016/0221261 A1 * 8/2016 Yamamoto ............. B29C 64/40

* cited by examiner

3D PRINTING OF COMPOSITION-CONTROLLED COPOLYMERS

RELATED APPLICATIONS

This application claims priority to provisional patent application 62/400,967, "Composition Controlled 3D Printing Using Photo-Polymerization," filed Sep. 28, 2016. The content of this provisional patent application is incorporated by reference.

BACKGROUND

Three-dimensional printing using polymerization is known. For example, U.S. Pat. No. 4,575,330 to Charles Hull discloses a system for iterative polymerization of a liquid. However, the system of the Hull patent results in a 3D object having a generally consistent composition. Later systems also are limited in the sense that the 3D objects they produce have a generally consistent composition.

SUMMARY

A computer-controlled method for forming a composition-controlled product using 3D printing includes disposing two or more liquid reactant compositions in respective two or more reservoirs; and mixing the two or more liquid reactant compositions, which in turn includes controlling by the computer a mass ratio of the mixed two or more liquid reactant compositions. The computer-controlled method further includes scanning, under control of the computer, a mixed liquid reactants nozzle over a substrate; depositing the mixed liquid reactant compositions onto the substrate; and operating, under control of the computer, a light source to polymerize the deposited mixed liquid reactant compositions.

In an embodiment of the method, the liquid reactant compositions in the reservoirs comprise reactant(s), initiators, porogenic particles, reinforcing particles, solvent(s), and combinations thereof. In an aspect, the reactants are chosen from a group consisting of monomers or monomer mixtures that form composition controlled copolymers at different degrees of monomer to polymer conversion. In an aspect, the initiators are chosen from a group consisting of initiators for free-radical polymerization, cationic polymerization or anionic polymerization. In an aspect, the porogenic particles are chosen from a group consisting of water soluble sugar or salt and organic solvent soluble polymer particles. In an aspect, the reinforcing particles are chosen from a group consisting of metal oxide particles and nanoparticles.

In an embodiment of the method, the mass fraction of liquid reactant is controlled by flow rate and mixed in a container within the nozzle or immediately adjacent to the nozzle. In an embodiment, the degree of monomer to polymer conversion is controlled using laser intensity and irradiation time. In an embodiment, the printed products are submitted to post printing treatments. In an aspect, the post printing treatments are chosen from a group consisting of soaking in water or aqueous solutions, soaking in organic solvents, and annealing.

In an embodiment, the method may be used for making dental devices for dental restorative material, denture, orthodontic treatment, dental implant, implant, tissue regeneration, and tissue engineering.

In an embodiment, the method may be used for making optical devices with spatially controlled optical properties, including refractive index, transmission, reflectance, color, polarization, and glossiness.

DESCRIPTION OF THE DRAWINGS

The detailed description refers to the following figures in which like numerals refer to like objects, and in which.

DETAILED DESCRIPTION

Disclosed is a novel and nonobvious 3D printing system and corresponding method or process that may be used to manipulate chemical, physical and mechanical properties at each 3D location of an object. In an embodiment, the 3D printing method includes the steps of preparing a reactants mixture, extruding the mixture through a scanning nozzle, and solidifying the mixture by photo-polymerization. The mixture may be prepared by blending two or more different reactant liquids supplied from separate reservoirs. The relative composition of each reactant liquid in the mixture may be controlled with a flow control unit installed between its reservoir and a blending unit. The composition-controlled reactant mixture may be extruded onto a substrate through a scanning nozzle with or without a separate flow controller. In an embodiment, as the mixture touches the substrate, the mixture is solidified rapidly by photo-polymerization with visible or UV light irradiation.

Using this 3D printing method, the chemical, physical, mechanical, and biological properties of a printed product can be controlled by various means including, but not limited to: (1) the relative compositions of reactants in the mixture; (2) the flow rate of the mixture liquid; (3) the intensity, irradiation time, and wavelength of photo-polymerizing light; and (4) the scanning nozzle velocity. Additional post-printing processes may be added to improve the final product properties, e.g., photo- or heat-annealing for leachable reactants removal.

The herein disclosed method for 3D printing of composition-controlled copolymers makes it possible for a single printing process to produce 3D products with complex geometries as well as to continuously or discretely control the chemical, physical and mechanical properties within the 3D product. The method also allows addition of solid dispersion components into the liquid mixture for specific applications, e.g., filler nanoparticles for dental materials. The photo-polymerized 3D products of the reactants may be durable and bio-compatible resin networks and composites.

Figure 1:
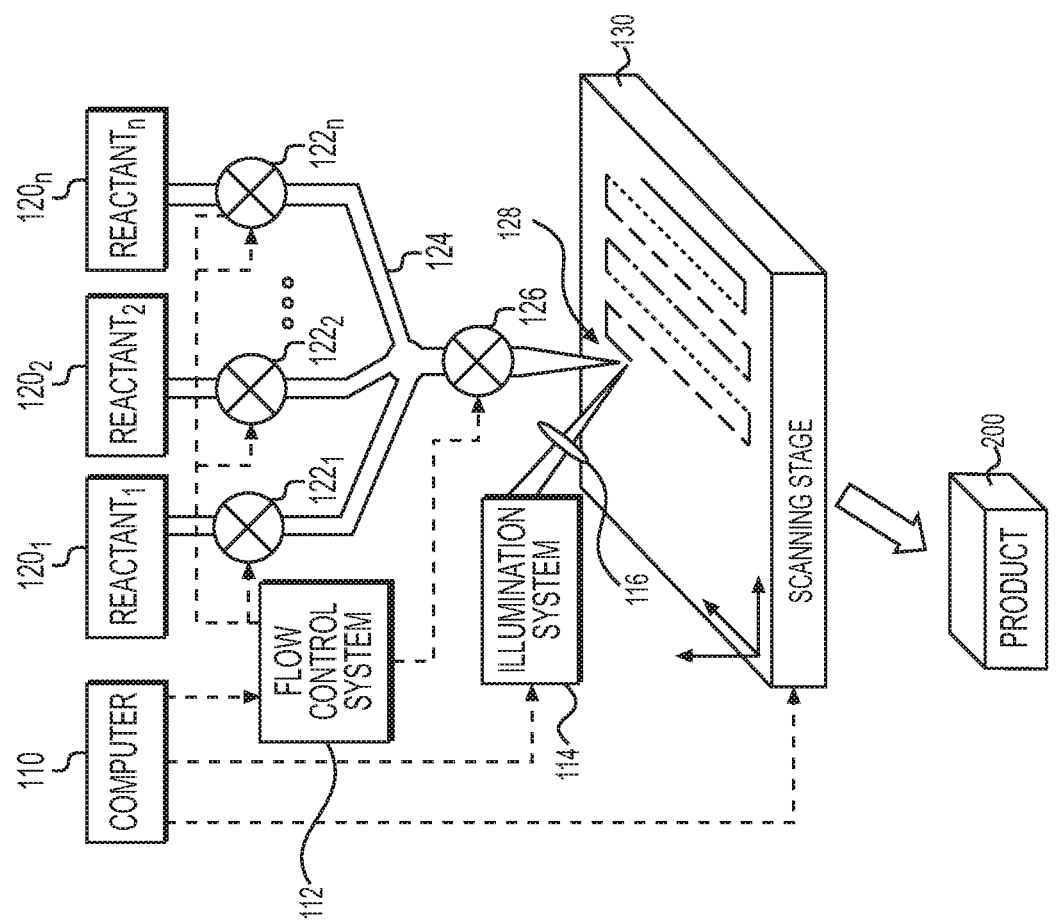
FIG. 1 illustrates an example system for 3D printing of composition-controlled copolymers.

FIG. 1 illustrates an example of a composition-controlled 3D printing system. In FIG. 1, composition-controlled 3D printing system 100 includes a liquid composition sub-system, a liquid flow control sub-system, a polymerizing sub-system, and a processor sub-system. The above sub-systems cooperate to produce 3D, composition-controlled product 200. More specifically, the system 100 includes computer 110 which may execute machine instructions to control specific components of the system 100, specifically flow control system 112, illumination system 114, and scanning stage 130. The flow control system 112 operates valves $122_i$ to control flow of reactant compositions from reservoirs $120_i$ into discharge component 124, and further operates mixing chamber and mixing valve 126 to control the rate of deposition of the blended reactant compositions through nozzle 128. The nozzle 128 deposits the blended reactant compositions onto scanning stage 130. The computer 110 further controls three-dimensional motion of the nozzle 128 as over a substrate placed on, or integral to, the scanning stage 130. Alternately, the nozzle 128 may be fixed, and the scanning stage 130 may be moved. The computer 110 still further controls illumination system 114, which may provide light (e.g., a laser) for curing the deposited, blended reactant compositions. The light provided by illumination system 114 may pass through lens component 114. The light may be applied in a step wise fashion as the 3D product is printed.

Figure 2A:
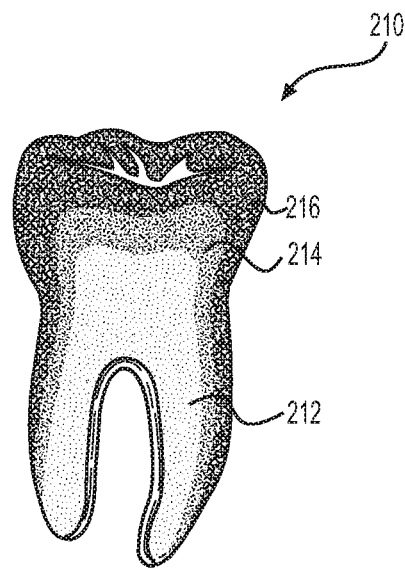
FIGS. 2A and 2B illustrate example 3D products printed by the system of FIG. 1.
Figure 2B:
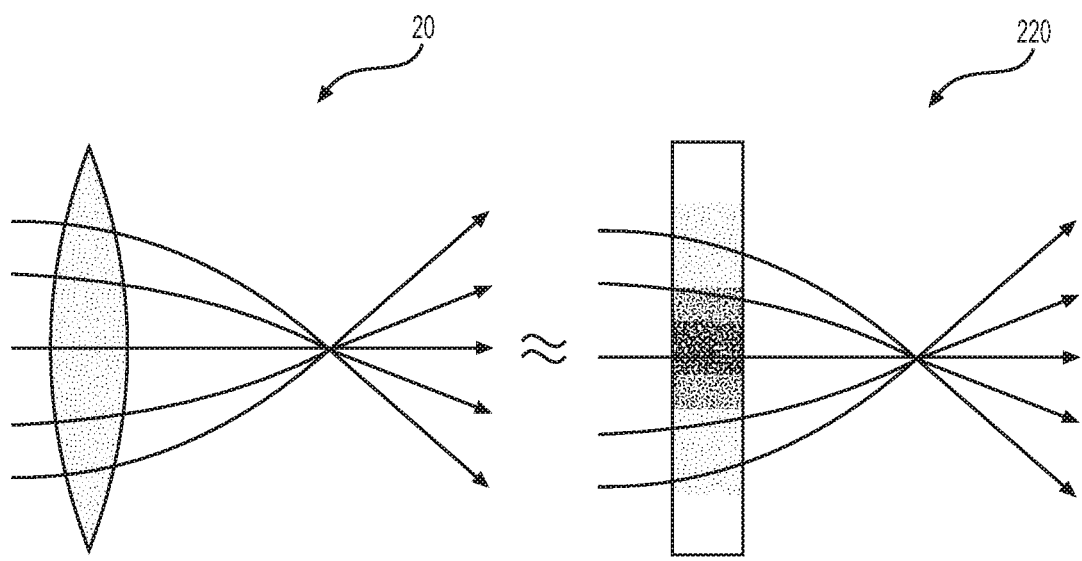

FIGS. 2A and 2B illustrate, respectively, 3D-printed products 210 and 220. Product 210 is an example 3D-printed tooth having a varying composition including layers 212, 214, and 216, as in an actual human tooth. Product 220 is an aberration-free single lens with gradient-index (GRIN) optics printed according to the herein disclosed concepts, and can be compared to conventionally-formed lens 20. See Example 16 of this disclosure.

Using the example system 100, the composition of liquid reactant mixtures may be controlled during 3D printing. Furthermore, the example system 100 allows the chemical, mechanical, and biological properties at all locations in a 3D product to be defined by changing relative compositions of reactants in the mixture, and by other means, as described in the example that follow. In addition, the chemical, physical, mechanical, and morphological properties of the 3D products may be optimized further by adding additional solid components into a reactant, such as fillers for dental products. Still further, the spatial resolution of the 3D products also may be adjusted by varying compositions of reactants with different rheological characteristics.

In an embodiment, the liquid reactant compositions in the reservoirs 120$_i$ include reactant(s), initiators, porogenic particles, reinforcing particles, solvent(s), and combinations thereof. In an aspect, the reactants are may be monomers or monomer mixtures that form composition controlled copolymers at different degrees of monomer to polymer conversion. In an aspect, the initiators may be initiators for free-radical polymerization, cationic polymerization or anionic polymerization. In an aspect, the porogenic particles may be water soluble sugar or salt and organic solvent soluble polymer particles. In an aspect, the reinforcing particles may be metal oxide particles and nanoparticles.

In an embodiment, the system 100 may be operated to vary the mass fraction of liquid reactant compositions by controlling flow rate from the reservoirs 120$_i$ and mixing in the nozzle 128. In an embodiment, the degree of monomer to polymer conversion is controlled using laser intensity and irradiation time of illumination system 114.

Once the 3D product 200 is produced, additional post-printing processes may be employed to improve the final product in terms of chemical, mechanical, or biological performance, e.g., by removal of leachable reactants in dentures and other medical devices. In an embodiment, the printed 3D products are submitted to post printing treatments. In an aspect, the post printing treatments include of soaking in water or aqueous solutions, soaking in organic solvents, and annealing.

In the examples that follow, the inventors used aspects of the above-described methods to create composition-controlled 3D products and to verify the properties of the 3D products. In the past, Raman and infra-red (IR) spectroscopy methods have been used to measure degree of vinyl conversion in photo-polymerization reactions. However, conventional spectroscopic methods are not sufficiently fast to monitor reactions on the millisecond (ms) scale, which is critical scale for practical 3D printing. Moreover, the "irreversible" nature of the photo-polymerization makes it impossible to perform a repetitive synchronized reaction monitoring.

To overcome the deficiencies of current Raman and IR spectroscopy methods, sensitive CARS spectroscopy can be used to monitor the photo-polymerization reaction. A visible light illuminates a localized area with a CARS signal collection objective lens. The illumination time and period are controlled by an electronic shutter with a millisecond (ms) opening/closing time. For example, CARS spectra can be collected every 10 ms to record changes in Raman spectra during the photo-polymerization reaction.

The inventors also devised a microscopy study by measuring the spatial profile of degree of conversion near the illuminated area. In this study, an 80 μm line scan measured spatially can resolve Raman spectra every second to monitor the spatial evolution of polymerization from the illuminated area. These data will help the inventors understand how best to control the spatial resolution of the 3D product.

Examples 1-16 provide various examples directed to the above-disclosed concepts envisaged by the inventors.

Example 1

Monomer Mixtures for Composition-Controlled Photo-Polymerization

In Example 1, two monomers with free-radical polymerizable vinyl groups were used as models. One monomer, triethylene glycol-divinylbenzyl ether (TEG-DVBE), was lab-prepared. TEG-DVBE is stable to hydrolysis and esterase degradation because of the ether-based chemical structure. The other monomer, urethane dimethacrylate (UDMA), is one of the key components in medical devices such as dental restorative materials used to treat carious teeth. The commercial monomer UDMA was supplied by Esstech (Essington, Pa., USA) and was used as received. TEG-DVBE was synthesized and fully characterized in house according to a previously reported procedure. The monomer mixtures were activated by 0.2 wt % of camphorquinone (CQ, Aldrich, St. Louis, Mo., USA) and 0.8 wt % of ethyl 4-N,N-dimethylaminobenzoate (amine, Aldrich, St' Louis, Mo.).

Photo-Polymerization Methods:

The monomer mixtures (10 μL) were sandwiched between two Mylar films, and photo-cured using a handheld dental curing light (SmartLite max LED curing light, model: 644050, Dentsply International, Milford, Del., USA). The intensity of light irradiation was adjusted through the distance of light to sample.

A unique feature of the monomer mixture of Example 1 is the azeotropic composition at equimolar TEG-DVBE and UDMA when CQ/amine are used as initiators. Azeotropic compositions in copolymers means that the mole fractions of the feed monomers are retained in the polymer and are constant throughout the polymerization process. The viscosity of the monomers plays an inconsequential role during the polymer chain propagation, considering that the viscosity of UDMA (6.7 Pa·s) (Pascal second) is approximately 240 time higher than that of TEG-DVBE (0.028 Pa·s).

Example 2

Monomer Mixtures for Composition Shift Photo-Polymerization

In contrast to Example 1, copolymerization of UDMA and triethylene glycol dimethacrylate (viscosity=0.012 Pa·s) showed significant composition drift when degree of conversion was above 20%. More diluting monomers that diffused quickly in the resin network converted into polymers at high degrees of vinyl conversion. This composition drift is due to the diffusion limitation when the mixture was vitrified upon polymerization. In general, the low viscosity monomers diffused faster and thus react to the active radicals more efficiently. Consequently, the low viscosity monomers converted into the polymer network more rapidly than did the high viscosity monomers.

Example 3

Monomer Mixtures with Solvents: Enhanced Ease of Handling

UDMA or other high viscosity monomer or monomer mixtures were dissolved in dichloromethane or other low boiling temperature solvents at 50% by mass. The UDMA solution was stored in one container, ready to be mixed with components from other containers, or to be printed out by itself.

Example 4

Mixtures of Monomers and Water Soluble Particles for Generating Porous Structures In one container, a monomer (for example, TEGDMA) was mixed with various mass fractions of metal particles or metal oxide particles (such as silica, alumina, and titania). The viscosity of this mixture was adjusted to flow through the nozzle. The mixture in this container was ready to be mixed with components from other containers or to be printed out by itself.

Example 5

Mixtures of Monomers and Particles to Provide a Broad Range of Mechanical Properties In one container, a monomer (for example, TEGDMA) was mixed with various mass fraction of water soluble particles including sugar and salt, or polymer particles (e.g., polystyrene particles) that may be dissolved by organic solvents. The viscosity of this mixture was adjusted to flow through the nozzle. The mixture in this container was ready to be mixed with components from other containers or to be printed out by itself.

Example 6

Composition of Monomer Mixtures Determines Mechanical Properties (Same Pair of Monomers with Different Mole Ratios)

By varying the mole ratio of UDMA and TEGDVBE, the mechanical properties of the 3D product, including elastic modulus and hardness, were changed accordingly. Using mole ratios at 3/1 and 1/1 as examples, the elastic modulus of the 3/1 mixture (1.78+/−0.04 GPa) was approximately 23% more than that of the 1/1 mixture (1.45+/−0.04 GPa) when their degree of vinyl conversion was 80%. Furthermore, the hardness of the 3/1 mixture (14.9+/−0.8) was 73% higher than that of the 1/1 mixture.

Flexural Modulus (E) and Flexural Strength (F) by 3-Point Bending:

To determine Flexural modulus (E) and flexural strength (F) six rectangular specimen bars were prepared by inserting a composite into a stainless-steel mold (25 mm×2 mm×2 mm) and covering the specimen surfaces with a Mylar film to prevent air-inhibited layers. The specimen bars were cured (2 min/each open side of the mold) using a Dentsply Triad 2000 visible light curing unit (Dentsply, York, Pa., USA) with a tungsten halogen light bulb (75 W and 120 V, 43 mW/cm$^2$). After curing, the specimen bars were stored at room temperature for 24 hours. The flexural modulus of the specimen bars was determined using the Universal Testing Machine (Instron 5500R, Instron Corp., Canton, Mass., USA) at a cross-head speed of 1 mm/min. The specimen bars were placed on a 3-point bending test device with a 20 mm distance between supports and an equally distributed load. The flexural modulus (E) and flexural strength (F) values were calculated following ISO4049: 2009 protocols/equations.

Knoop Hardness (HK):

A microhardness machine (Wilson Tukon 2100; Instron Corp., Canton, Mass., USA) with indentation loads of (0.25-5) N was used for HK measurements (ASTM standard E 384). The loading time for an indentation was 15 seconds with a dwell at peak load of 15 seconds. Indentation sizes were measured with a 10× or a 50× objective. The HK values were calculated by dividing a test force by the indentation projected surface area. The reported HK values represent the average of five repetitive measurements. The standard uncertainty associated with the HK measurements was 5%.

Example 7

Composition of Monomer Mixtures Determines Mechanical Properties (Different Pairs of Monomers)

In this example, the mechanical properties in terms of E and HK of equimolar mixtures of UDMA/TEGDVBE and UDMA/TEGDMA were evaluated. The mixture containing TEGDMA had a flexural modulus (E) pf (2.37+/−0.04 GPa) and HK of (13.6+/−1.0), which were 63% and 48% higher, respectively, than those values for TEGDVBE.

Example 8

Composition of Monomer Mixtures Determines Mechanical Properties (with Fillers)

The addition of fillers significantly enhanced the mechanical properties. The flexural modulus (E) of composites with 75 wt % fillers was 5.6 and 4.1 times more rigid in comparison to the TEGDVBE containing and TEGDMA containing resins in Example 7, respectively.

Example 9

Control Composition of Monomer Mixtures by Changing the Flow Rate of Liquids Through the Nozzles In this example, the composition of monomer mixtures may be varied by changing the flow rate of liquids from different containers. The amount of liquids from the containers may be controlled through the flow rate to the mixing unit where the liquids are mixed.

Example 10

Degree of Vinyl Conversion (DC) Determines Mechanical Properties

Using equimolar UDMA/TEGDVBE resin as an example, when the DC of this resin increased from 80% to 99%, its flexural modulus was increased to 70%. The flexural modulus of equimolus UDMA/TEGDMA was increased to 41% for the same amount of DC increase.

Determine the Degree of Vinyl Conversion (DC) Using FTIR-ATR and Peak Fitting Methods.

The degree of vinyl conversion (DC) was evaluated immediately after curing using a Thermo Nicolet Nexus 670 FT-IR spectrometer (Thermo Scientific, Madison, Wis., USA) with a KBr beamsplitter, an MCT/A detector and an attenuated total reflectance (ATR) accessory. The areas of absorption peaks of the vinyl group of TEG-DVBE at 1629 $cm^{-1}$, and the methacrylate groups of UDMA at 1638 $cm^{-1}$ were integrated, and the degree of conversion was calculated using the aromatic group of TEG-DVBE at 1582 $cm^{-1}$ or the amide group of UDMA at 1537 $cm^{-1}$ as an internal standard. Peaks were resolved with the assistance of the curve fitting program Fityk (version 0.9.8). To correct any potential discrepancy, a standard curve was produced by plotting varied resin composition ratio values analyzed by NMR spectroscopy against the values obtained through FTIR peak fitting. The phenyl absorbance at 1612 $cm^{-1}$ was the internal standard for TEG-DVBE homo-polymers. The degree of vinyl conversion (DC) was calculated according to the following equation: $DC=(A1/A0-A1'/A0')/(A1/A0')$ 100%, where A1/A0 and A1'/A0' stand for the peak-area-ratio of the vinyl-of-interest and internal standard before and after polymerization, respectively. The vinyl-of-interest may be vinyl groups from TEG-DVBE, UDMA, or both.

Example 11

Control the Degree of Vinyl Conversion (DC) Through Light Intensity and Irradiation Time Real-time Raman micro-spectroscopy further confirmed that the equimolar composition of UDMA/TEGDVBE was constant over time during photo-polymerization and was independent of the polymerization rate, which was controlled through light intensity and irradiation time. To achieve a step-wise polymerization, specimens were exposed to light at 4 $mW/cm^2$ for 5 seconds up to a total of four exposures. The classical least squares (CLS) method was used from pure monomer spectra to estimate unpolymerized monomer composition in the samples using the C=C stretching bands of TEG-DVBE and UDMA. CLS scores for each specimen were normalized to 100 for the pre-polymerized monomer mixtures. As the vinyl groups converted to polymers, the associated C=C band intensity decreased, and the degree of vinyl conversion (DC) increased accordingly. At each light irradiation, the intensity dropped immediately, and then decreased at a much slower rate, before the next irradiation. During the full time range (10 min) of this set of experiments, DC reached approximately 20%, and the ratio of TEG-DVBE/UDMA was always 1/1. A faster photo-polymerization took place when the sample was irradiated at 150 $mW/cm^2$ for 20 seconds. The DC of this specimen reaches approximately 55% immediately after light irradiation. At this DC, the resin was cured. With light intensity at 1000 $mW/cm^2$, the DC reached 90% within seconds. During the course of this set of experiments, the ratio of TEG-DVBE and UDMA was always 1/1.

Example 12

Chemical Composition of Copolymers Determines the Refractive Index

The refractive index of UDMA/TEGDVBE mixtures was linearly correlated with the mole fraction of the monomers: $y=0.6x+1.510$ ($R2=0.996$), where y is the refractive index of the mixture, and x is the mole fraction of TEGDVBE. The refractive index of UDMA, TEGDVBE, and an equimolar mixture of these two was 1.510, 1.571, and 1.528, respectively.

Refractive Indexes (n):

The n of copolymers and their corresponding composites were measured by matching with the refractive index liquids (interval of $n=0.004$, Cargille Labs Inc., N.J., USA) at 22° C. The value of matched n was based upon OLYMPUS BX50 light microscope (OLYMPUS, Tokyo, Japan) observations when the specimen and the n-liquid were indistinguishable.

Example 13

3D Object with Variant Chemical Compositions

The chemical composition is defined as composition of cured copolymer, and the degree of vinyl conversion of the cured copolymer. The chemical composition may be modified by varying the flow rate of liquids from different containers, the irradiation intensity and duration, and post light-curing process.

Example 14

Post Cure Treatment By Annealing

After light curing, the 3D product may be subjected to annealing at varying temperatures based on the glass transition temperature of the resin network. This annealing process generates slight movement within the resin network, and thus fine tunes the 3D geometry and the mechanical properties as mentioned in the examples above.

Example 15

3D Product with Porous Structures—Dissolving Fillers After Curing

The 3D product was prepared using activated TEGDMA (with initiator CQ/amine) in one container and TEGDMA blended with sieved NaCl crystals in a second container. The mass fraction of NaCl in the porous region was set between 60 to 84% to achieve optimal porosity and strength. After the product was printed out and cured, the 3D product was soaked in deionized water for 5 days with multiple changes of water to dissolve the salt porogen, and then was air dried. The NaCl particles were successfully removed. The pore size of the 3D product matched the size of the NaCl particles. The porosity of the 3D product agreed well with the mass fraction of the NaCl added.

Example 16

3D Programmed Gradient-Index (GRIN) Optics

Gradient-index (GRIN) optics are a type of optics with a gradual change of the refractive index of a material. Such variation is used to produce lenses with flat surfaces or spherical lenses without aberrations. A spherical lens is inexpensive to fabricate compared to an aspherical lens. However, due to inherent spherical aberration, a spherical lens cannot be used alone for a high performance optical instrument. An aspherical lens or a complex lens (multiple lenses with different curvatures and refractive indices) may be used as an alternative. However, the production cost of these complex lenses is much higher than a single spherical lens, and the complex lenses have other unwanted optical limitations, such as limited numerical aperture, overall optics thickness, and reduced transmission. A GRIN lens can reduce spherical aberration of a single spherical lens or even a lens with a flat geometry. It is very challenging to reproducibly control the optical property of a conventional GRIN lens. A recent technology based on two-photon polymerization can fabricate a 3D lithographic controlled GRIN optics. However, its cross-linking based control of the refractive index is limited in the range of refractive index variation (e.g., $\Delta n=0.01$) and in the long-term product stability due to slow conversion of unreacted monomers. GRIN optics made by the using the herein disclosed concepts have a wider range of refractive index variation (e.g., $\Delta n=0.06$, from Example 12) and a much longer performance stability by controlling the ratios of fully converted compositions. In addition to refractive index for GRIN optics, 3D programmed optics made by using the herein disclosed concepts can have precisely controlled other optical properties, including transmission, reflectance, color, and glossiness. The spatial control can be radial, spherical, linear, or axial, depending on the intended optical properties.

The herein disclosed methods can be implemented as operations performed by a processor on data stored on one or more computer-readable storage devices or received from other sources. A computer program (also known as a program, module, engine, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network

We claim:

1. A computer-controlled method for forming a composition-controlled product using 3D printing, comprising:
    disposing two or more liquid reactant compositions in respective two or more reservoirs;
    mixing the two or more liquid reactant compositions, comprising controlling by the computer a mass ratio of the mixed two or more liquid reactant compositions;
    scanning, under control of the computer, a mixed liquid reactants nozzle over a substrate;
    depositing the mixed liquid reactant compositions onto the substrate; and
    operating, under control of the computer, a light source to polymerize the deposited mixed liquid reactant compositions, comprising, throughout the entire method for forming the composition-controlled product, as the deposited mixed liquid reactant compositions touch the substrate, operating the light source to rapidly polymerize the compositions.

2. The method of claim 1, wherein the liquid reactant compositions in the reservoirs comprise reactant(s), initiators, porogenic particles, reinforcing particles, solvent(s), and combinations thereof.

3. The method of claim 2, wherein the reactants are chosen from a group consisting of monomers or monomer mixtures that form composition controlled copolymers at different degrees of monomer to polymer conversion.

4. The method of claim 2, wherein the initiators are chosen from a group consisting of initiators for free-radical polymerization, cationic polymerization or anionic polymerization.

5. The method of claim 2, wherein the porogenic particles are chosen from a group consisting of water soluble sugar or salt and organic solvent soluble polymer particles.

6. The method of claim 2, wherein the reinforcing particles are chosen from a group consisting of metal oxide particles and nanoparticles.

7. The method of claim 1, wherein the mass fraction of liquid reactant is controlled by flow rate and mixed in a container within the nozzle.

8. The method of claim 1, wherein the degree of monomer to polymer conversion is controlled using laser intensity and irradiation time.

9. The method of claim 1, comprising, submitting printed products to post printing treatments.

10. The method of claim 9, wherein the post printing treatments are chosen from a group consisting of soaking in water or aqueous solutions, soaking in organic solvents, and annealing.

11. The method of claim 1, wherein printed products include dental devices for dental restorative material, denture, orthodontic treatment, dental implant, dental tissue regeneration, and dental tissue engineering.

12. The method of claim 1, wherein printed products include optical devices with spatially controlled optical properties, including refractive index, transmission, reflectance, color, polarization, and glossiness.

13. A method for composition-controlled printing of a 3D object, comprising:
    disposing each of a plurality of different liquid reactant compositions in respective ones of a plurality of reservoirs;
    controlling, by a computer, flows of the different liquid reactant compositions from the reservoirs into a mixing device, comprising:
        controlling, by the computer, a composition percentage of each of the different liquid reactant compositions in the mixing device comprising individually adjusting a flow from each of the respective ones of the reservoirs;

mixing homogeneously, the different liquid reactant compositions in the mixing device; and controlling, by the computer, mechanical properties of the 3D printed object by a plurality of step-wise depositions and polymerizations of the homogeneously mixed liquid reactant compositions, comprising:

depositing variable amounts of the homogeneously-mixed liquid reactant compositions onto a substrate using a scanning nozzle under control of the computer comprising controlling a flow from the mixing device, and polymerizing the deposited variable amounts of the homogeneously mixed liquid reactant compositions using a light source under control of the computer comprising throughout the composition-controlled product method as the deposited mixed liquid reactant compositions touch the substrate, operating the light source to rapidly polymerize the compositions.

14. The method of claim 13, wherein controlling, by the computer, a composition percentage comprises controlling one or more of a weight percentage, a volume percentage, and a molar ratio percentage of each of the different liquid reactants in the mixing device.

15. The method of claim 13, wherein the liquid reactant compositions form azeotropic compositions, and wherein controlling the mechanical properties of the 3D printed object comprises adjusting individually flows from the respective reservoirs to achieve a desired molar ratio of the different liquid reactants in the mixing device.

16. The method of claim 13, wherein controlling the mechanical properties of the 3D printed object comprises adjusting the variable amounts during one or more of the step-wise depositions and polymerizations.

17. The method of claim 13, wherein controlling the mechanical properties of the 3D printed object comprises adjusting the intensity and duration of the light source during one or more of the step-wise depositions and polymerizations.

18. The method of claim 13, comprising:
disposing dissolvable fillers in one or more of the different liquid reactant compositions;
curing the printed 3D object; and
dissolving the dissolvable fillers to produce porosities in the printed 3D object.

19. The method of claim 1, wherein the mass fraction of liquid reactant is controlled by flow rate and mixed in a container immediately adjacent to the nozzle.

* * * * *

UNITED STATES PATENT AND TRADEMARK OFFICE
CERTIFICATE OF CORRECTION

PATENT NO. : 10,625,470 B2
APPLICATION NO. : 15/702779
DATED : April 21, 2020
INVENTOR(S) : Jirun Sun et al.

Page 1 of 1

It is certified that error appears in the above-identified patent and that said Letters Patent is hereby corrected as shown below:

In the Specification

Column 1, Line 12, The following should appear, after the paragraph titled "RELATED APPLICATIONS,":
STATEMENT OF FEDERALLY SPONSORED RESEARCH
This invention was made with government support under grant U01 DE023752 awarded by the National Institutes of Health. The government has certain rights in the invention.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*